US012624323B2

(12) United States Patent
Horii et al.

(10) Patent No.: US 12,624,323 B2
(45) Date of Patent: May 12, 2026

(54) MULTILAYER CULTURE VESSEL

(71) Applicant: Sinfonia Technology Co., Ltd., Tokyo (JP)

(72) Inventors: Daichi Horii, Tokyo (JP); Haruki Takeuchi, Tokyo (JP)

(73) Assignee: Sinfonia Technology Co., Ltd., Tokyo (JP)

( * ) Notice: Subject to any disclaimer, the term of this patent is extended or adjusted under 35 U.S.C. 154(b) by 867 days.

(21) Appl. No.: 17/619,744

(22) PCT Filed: Jun. 15, 2020

(86) PCT No.: PCT/JP2020/023460
§ 371 (c)(1),
(2) Date: Dec. 16, 2021

(87) PCT Pub. No.: WO2020/255928
PCT Pub. Date: Dec. 24, 2020

(65) Prior Publication Data
US 2022/0356427 A1 Nov. 10, 2022

(30) Foreign Application Priority Data

Jun. 17, 2019 (JP) ................................. 2019-112230

(51) Int. Cl.
| | |
|---|---|
| *C12M 1/24* | (2006.01) |
| *C12M 1/00* | (2006.01) |
| *C12M 1/12* | (2006.01) |

(52) U.S. Cl.
CPC ............ *C12M 23/04* (2013.01); *C12M 23/34* (2013.01); *C12M 27/22* (2013.01)

(58) Field of Classification Search
CPC ....... C12M 23/04; C12M 23/08; C12M 23/34
See application file for complete search history.

(56) References Cited

U.S. PATENT DOCUMENTS

| | | |
|---|---|---|
| 2008/0206857 A1 | 8/2008 | Kenney et al. |
| 2010/0129900 A1 | 5/2010 | Clark et al. |

(Continued)

FOREIGN PATENT DOCUMENTS

| | | |
|---|---|---|
| CN | 102099459 A | 6/2011 |
| JP | S52145590 A | 12/1977 |

(Continued)

OTHER PUBLICATIONS

China Patent Application No. 2020800440081, Office Action, dated Sep. 5, 2023.

(Continued)

*Primary Examiner* — Jonathan M Hurst
(74) *Attorney, Agent, or Firm* — Kilpatrick Townsend & Stockton LLP

(57) ABSTRACT

A multilayer culture vessel includes: an internal space that is divided by a boundary portion into a culture space on one side and a buffer space on the other side in a direction parallel to a bottom plate; at least one intermediate plate extending along the direction parallel to the bottom plate at least in the culture space and configured to divide the culture space into culture layers; wall portions at the boundary portion, the wall portions including one extending from the bottom plate in a direction toward a top plate and one extending from each of the at least one intermediate plate in a direction toward the top plate; communication portions formed at the boundary portion to bring the culture layers into communication with the buffer space; and a liquid supply/drainage port formed in the housing at a location facing the buffer space.

8 Claims, 7 Drawing Sheets

(56)              References Cited

U.S. PATENT DOCUMENTS

| | | | |
|---|---|---|---|
| 2011/0020923 A1* | 1/2011 | Lacey | C12M 23/34 |
| | | | 435/304.2 |
| 2014/0120607 A1 | 5/2014 | Abraham | |
| 2014/0120608 A1 | 5/2014 | Carter et al. | |
| 2016/0137961 A2 | 5/2016 | Clark et al. | |

FOREIGN PATENT DOCUMENTS

| | | |
|---|---|---|
| JP | 2011024577 A | 2/2011 |
| JP | 2018138056 A | 9/2018 |
| WO | 2010008566 A2 | 1/2010 |

OTHER PUBLICATIONS

International Patent Application No. PCT/JP2020/023460, Search Report (and English translation) and Written Opinion, dated Sep. 1, 2020.
Europe Patent Application No. 20827007.4, Search Report, dated Jul. 27, 2023.

* cited by examiner

One side $\longleftrightarrow$ The other side

One side ⟵⟶ The other side

One side $\longleftrightarrow$ The other side

One side $\longleftarrow$ $\longrightarrow$ The other side

MULTILAYER CULTURE VESSEL

CROSS-REFERENCE TO RELATED APPLICATIONS

This application is a national stage application of International Patent Application No. PCT/JP2020/023460, filed on Jun. 15, 2020, which claims priority to Japan Patent Application No. 2019-112230, filed on Jun. 17, 2019, both of which are hereby incorporated by reference in their entireties.

TECHNICAL FIELD

The present disclosure relates to a multilayer culture vessel capable of culturing cells in multiple culture layers.

BACKGROUND

There are several types of cell culture methods. The most common method is static culture in which cells are cultured while adhering to a culture vessel. Specifically, cells are brought into close contact with a bottom surface of a culture vessel such as a petri dish or a culture flask, a medium is added to a culture layer formed by the bottom surface and a side surface of the culture vessel, and cell culture is performed under predetermined environmental conditions. As the culture progresses, cells proliferate along the bottom surface of the culture vessel. Further, in recent years, in order to perform static culture for a large amount of cells, there has been developed a multilayer culture vessel that has a plurality of adherence surfaces to which cells can adhere and includes a plurality of culture layers formed therein (see FIG. 6).

In the static culture, when performing subculture in which proliferated cells are transferred to a new culture vessel or when recovering cultured cells, it is necessary to peel the cells from the adherence surfaces with a peeling liquid. In particular, when cell peeling is performed on the multilayer culture vessel, it is required to supply a large amount of peeling liquid, and it is necessary to distribute the supplied peeling liquid to the respective culture layers inside the culture vessel by a predetermined procedure. For example, as shown in FIG. 6, a conventional multilayer culture vessel 201 includes a rectangular parallelepiped housing composed of a bottom plate 202, a top plate 203, and a side wall 204, a plurality of intermediate plates 205 configured to divide the internal space of the housing into a plurality of culture layers 221, a liquid supply/drainage part 206 configured to supply and drain a liquid to and from the multilayer culture vessel 201, and an exhaust port 207 configured to discharge a gas inside the housing. The liquid supply/drainage part 206 has a cylindrical shape in which the top plate 203 side is opened and which penetrates the plurality of intermediate plates 205 from the top plate 203 side to the bottom plate 202 side. A plurality of communication portions 214 in communication with the respective culture layers 221 is formed on the cylindrical side surface of the liquid supply/drainage part 206. Further, as shown in FIG. 6, the opening portion of the liquid supply/drainage part 206 is arranged at the corner of the top plate 203, and the exhaust port 207 is arranged at the corner adjacent to the arrangement position of the liquid supply/drainage part 206. The procedure for supplying a peeling liquid 30 to the conventional multilayer culture vessel 201 and peeling the cells will be described below with reference to FIGS. 7A to 7D. The hatched portion in FIGS. 7A to 7D is a region where the peeling liquid 30 exists.

First, as shown in FIG. 7A, the multilayer culture vessel 201 is arranged so that the liquid supply/drainage part 206 is located on the bottom side with the exhaust port 207 located on the top side and the bottom plate 202 is perpendicular to a horizontal mounting surface (hereinafter referred to as first posture), and the medium inside the multilayer culture vessel 201 is drained from the liquid supply/drainage part 206. Subsequently, in the state in which the multilayer culture vessel 201 is arranged at the first posture, a predetermined amount of the peeling liquid 30 is supplied from the liquid supply/drainage part 206 to the inside of the multilayer culture vessel 201. After the peeling liquid 30 is supplied, as shown in FIG. 7B, the multilayer culture vessel 201 is re-arranged so that the liquid supply/drainage part 206 and the exhaust port 207 are located on the top side while the bottom plate 202 is kept perpendicular to the mounting surface (hereinafter referred to as second posture). As a result, the peeling liquid 30 flows into the respective culture layers 221 substantially evenly via the communication portions 214. Next, as shown in FIG. 7C, the multilayer culture vessel 201 is re-arranged so that the bottom plate 202 comes into contact with the mounting surface and the liquid supply/drainage part 206 and the exhaust port 207 are located on the top side (third posture). As a result, the peeling liquid 30 spreads uniformly along the bottom plate 202 and the intermediate plates 205, and the entire cells adhering to the bottom plate 202 and the intermediate plates 205 are immersed in the peeling liquid 30. Then, by leaving the multilayer culture vessel 201 at the third posture for a predetermined time, the cells are peeled from the bottom plate 202 and the intermediate plates 205. Finally, as shown in FIG. 7D, the multilayer culture vessel 201 is arranged at the first posture again, and the cells peeled from the bottom plate 202 and the intermediate plates 205 are discharged from the liquid supply/drainage part 206.

By the procedure described above, it is possible to recover the cells peeled from the bottom plate 202 and the intermediate plates 205 in the conventional multilayer culture vessel 201. However, as shown in FIG. 7A, the peeling liquid 30 flows into the respective culture layers 221 while the multilayer culture vessel 201 is arranged at the first posture and the peeling liquid 30 is supplied to the multilayer culture vessel 201. Therefore, when the multilayer culture vessel 201 is arranged at the first posture, the cells adhering to the bottom plate 202 and the intermediate plates 205 near the side wall 204 located on the bottom side are immersed in the peeling liquid 30 throughout the supply of the peeling liquid 30. On the other hand, when the multilayer culture vessel 201 is arranged at the first posture, the cells adhering to the bottom plate 202 and the intermediate plates 205 near the side wall 204 located on the top side are not immersed in the peeling liquid 30 while supplying the peeling liquid 30. Since it takes time to supply a large amount of peeling liquid into the vessel, in the conventional multilayer culture vessel 201, the time for the cells to be immersed in the peeling liquid varies depending on the location. When the time for the cells to be immersed in the peeling liquid is too long, the cells may be damaged. When the time for the cells to be immersed in the peeling liquid is too short, the cells cannot be peeled from the culture layers.

The present disclosure provides some embodiments of a multilayer culture vessel capable of suppressing variations in the time for cells to be immersed in a peeling liquid when the cells are peeled from culture layers.

SUMMARY

According to one embodiment of the present disclosure, there is provided a multilayer culture vessel capable of culturing cells in a plurality of culture layers. The multilayer culture vessel includes: a housing including a bottom plate, a top plate facing the bottom plate, and a plurality of side walls connecting the bottom plate and the top plate; a boundary portion that divides an internal space of the housing into a culture space on one side of the boundary portion and a buffer space on the other side of the boundary portion in a direction parallel to the bottom plate; at least one intermediate plate extending along the direction parallel to the bottom plate at least in the culture space and configured to divide the culture space into the plurality of culture layers; a plurality of wall portions at the boundary portion, the plurality of wall portions including one extending from the bottom plate in a direction toward the top plate and one extending from each of the at least one intermediate plate in a direction toward the top plate; a plurality of communication portions formed at the boundary portion to bring the culture layers into communication with the buffer space; and a liquid supply/drainage port formed in the housing at a location facing the buffer space.

By using the multilayer culture vessel described above, a peeling liquid can be supplied to the respective culture layers by the following procedure. First, the multilayer culture vessel is arranged on a mounting surface so that the side wall on the other side is located on the bottom side, i.e., so that the buffer space is located on the bottom side. Subsequently, the peeling liquid is supplied to the buffer space from the liquid supply/drainage port. After the peeling liquid is supplied, the multilayer culture vessel is re-arranged on the mounting surface so that the side wall connected to the side wall on the other side is located on the bottom side, i.e., so that the bottom plate and the intermediate plate are arranged side by side in a horizontal direction. Thus, a part of the peeling liquid inside the buffer space flows into the respective culture layers substantially evenly via the communication portions. Next, the multilayer culture vessel is re-arranged on the mounting surface so that the side wall on one side is located on the bottom side, i.e., so that the culture space is located on the bottom side. Thus, the entire peeling liquid in the buffer space flows into the respective culture layers substantially evenly via the communication portions. Finally, when the multilayer culture vessel is arranged so that the bottom plate is located on the bottom side, the peeling liquid in the respective culture layers spreads uniformly along the bottom plate or the intermediate plate.

According to the procedure described above, while the peeling liquid is being supplied from the liquid supply/drainage port, the peeling liquid flows into the buffer space and does not flow into the respective culture layers. Further, when the multilayer culture vessel is re-arranged twice after the supply of the peeling liquid, the peeling liquid exists only in a partial region of each of the culture layers. However, such a rearranging work can be completed in a short time. Therefore, the effect of time variance for the cells at different locations to be immersed in the peeling liquid is small. That is, according to the present disclosure, by providing the buffer space for temporarily storing the peeling liquid when supplying the peeling liquid, it is possible to suppress the variations in the time for the cells to be immersed in the peeling liquid.

Further, it is preferable that the multilayer culture vessel further includes an inclined plate extending from an upper end of the wall portion formed on the bottom plate toward the side wall that is on the other side of the boundary portion while being inclined toward the top plate.

The peeling liquid stored in the buffer space then flows into the respective culture layers via the communication portions. At this time, when a wall portion is provided on the bottom plate, a part of the peeling liquid remains in a portion of the buffer space surrounded by the wall portion, the bottom plate, and the side surface on the other side. Therefore, in the above configuration, there is provided the inclined plate extending from the upper end of the wall portion provided on the bottom plate toward the side wall on the other side while being inclined toward the top plate. As a result, the peeling liquid remaining in the buffer space flows into the culture layer between the bottom plate and the intermediate plate along the inclined plate. Therefore, the peeling liquid remaining in the buffer space can be reduced, and the peeling liquid can be used without waste.

Further, in the multilayer culture vessel, it is preferable that the at least one intermediate plate extends to the boundary portion in the culture space.

In the conventional multilayer culture vessel, the culture layers are completely separated from one another by the intermediate plates. Therefore, in order to supply the peeling liquid to the respective culture layers, it is necessary to provide the liquid supply/drainage part that has a cylindrical shape penetrating the intermediate plates and includes the plurality of communication portions formed on the cylindrical side surface to communicate with the respective culture layers. In contrast, in the above configuration, the intermediate plate extends to the boundary portion in the culture space on one side and does not extend to the buffer space on the other side. That is, the buffer space is not separated by the intermediate plate. The peeling liquid supplied to the buffer space can flow into the respective culture layers via the communication portions formed at the boundary portion. Therefore, according to the above configuration, in order to supply the peeling liquid to the respective culture layers, it is sufficient to merely form an opening (liquid supply/drainage port) at a location facing the buffer space of the housing. The multilayer culture vessel can be easily manufactured as compared with the conventional multilayer culture vessel which needs to form the cylindrical liquid supply/drainage part penetrating the intermediate plate.

Further, in the multilayer culture vessel, it is preferable that the at least one intermediate plate extends along the direction parallel to the bottom plate in both the culture space and the buffer space to divide the buffer space into a plurality of buffer layers, and that a through-hole penetrating the at least one intermediate plate be formed in the buffer space.

In the above configuration, the buffer space is divided into the plurality of buffer layers corresponding to the culture layers by the intermediate plate extending to the side wall on the other side. Further, since the through-hole is formed in the intermediate plate, a liquid or a gas can flow between the buffer layers. Therefore, when the peeling liquid is supplied to the buffer space and then the multilayer culture vessel is re-arranged so that the side wall connected to the side wall on the other side is located on the bottom side, a part of the peeling liquid flows into the respective culture layers substantially evenly while the remaining part of the peeling liquid is divisionally supplied into the buffer layers substantially evenly and stored in the buffer layers. From this state, when the multilayer culture vessel is re-arranged so that the culture space is located on the bottom side, the remaining part of the peeling liquid stored substantially evenly in the respective buffer layers flows into the respective culture layers via the communication portions. Accordingly, the entire peeling liquid can be more evenly supplied to the respective culture layers.

According to the present disclosure, it is possible to provide a multilayer culture vessel capable of suppressing variations in time for cells to be immersed in a peeling liquid when the cells are peeled from culture layers.

DETAILED DESCRIPTION

Preferred embodiments of the present disclosure will now be described in detail with reference to the accompanying drawings.

Figure 1:
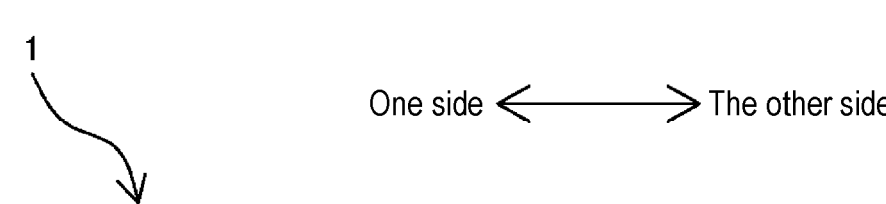
FIG. 1 is a perspective view showing a multilayer culture vessel according to an embodiment of the present disclosure.
Figure 1:
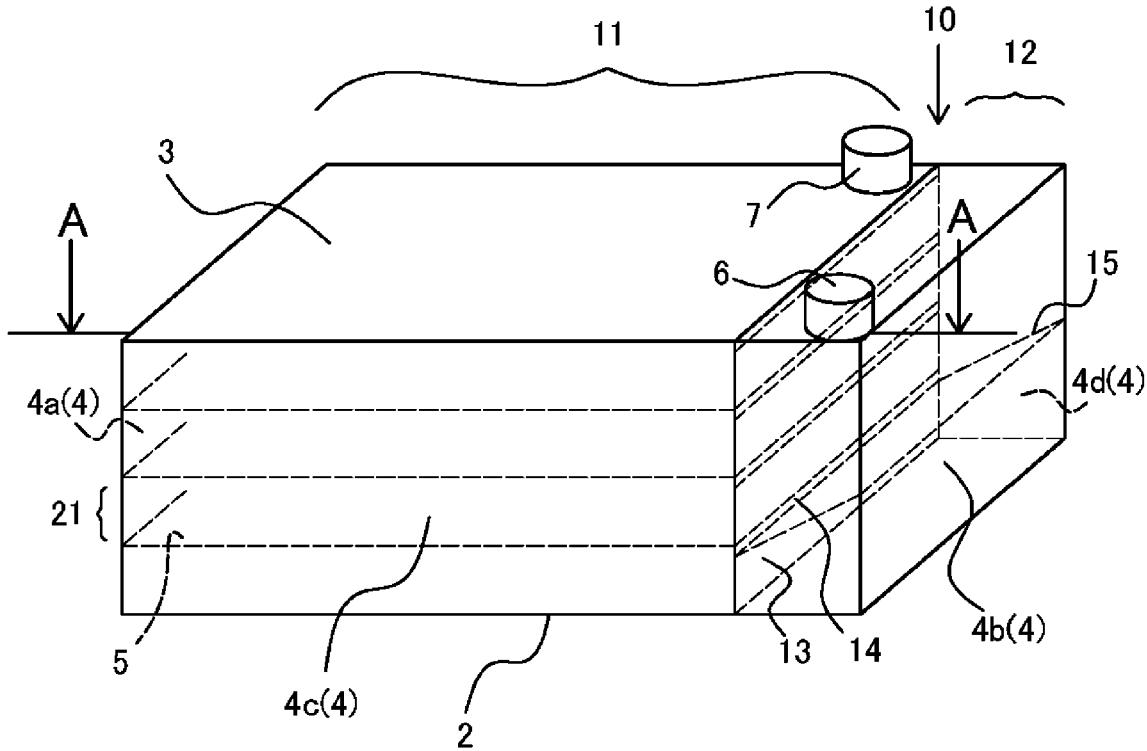

A multilayer culture vessel 1 according to the present embodiment is a rectangular parallelepiped-shaped culture vessel capable of culturing cells in a plurality of culture layers. As shown in FIG. 1, the multilayer culture vessel 1 includes a bottom plate 2, a top plate 3 facing the bottom plate 2, four side walls 4 connecting the bottom plate 2 and the top plate 3, three intermediate plates 5, a liquid supply/drainage port 6, and an exhaust port 7. Further, the internal space of the multilayer culture vessel 1 is divided into a culture space 11 on one side (the left-hand side in FIG. 1) of a boundary surface (boundary portion) 10 and a buffer space 12 on the other side (the right-hand side in FIG. 1) of the boundary surface 10 in a direction parallel to the bottom plate 2 (in a left-right direction in FIG. 1).

The bottom plate 2 and the top plate 3 are rectangular flat plates. The bottom plate 2 and the top plate 3 face each other. Further, the bottom plate 2 and the top plate 3 are connected by the four side walls 4. The side walls 4 includes a side wall 4a on one side, a side wall 4b on the other side, and side walls 4c and 4d connected to the side walls 4a and 4b.

The intermediate plates 5 extend in the direction parallel to the bottom plate 2 inside the culture space 11 and make contact with inner surfaces of the side walls 4a, 4c, and 4d. Further, the three intermediate plates 5 are arranged one above another in a direction perpendicular to the bottom plate 2. Cells may adhere to the bottom plate 2 and the intermediate plates 5. At the boundary surface 10, there are formed wall portions 13 including one extending from the bottom plate 2 in a direction toward the top plate and one extending from each of the three intermediate plates 5 in a direction toward the top plate 3, respectively. The region surrounded by the bottom plate 2, one intermediate plate 5, the side walls 4a, 4c and 4d, and one wall portion 13, the regions surrounded by two intermediate plates 5, the side walls 4a, 4c and 4d, and one wall portion 13, and the region surrounded by one intermediate plate 5, the top plate 3, the side walls 4a, 4c and 4d, and one wall portion 13 constitute culture layers 21, respectively. That is, four culture layers 21 are formed in the multilayer culture vessel 1 of the present embodiment.

Figure 2:
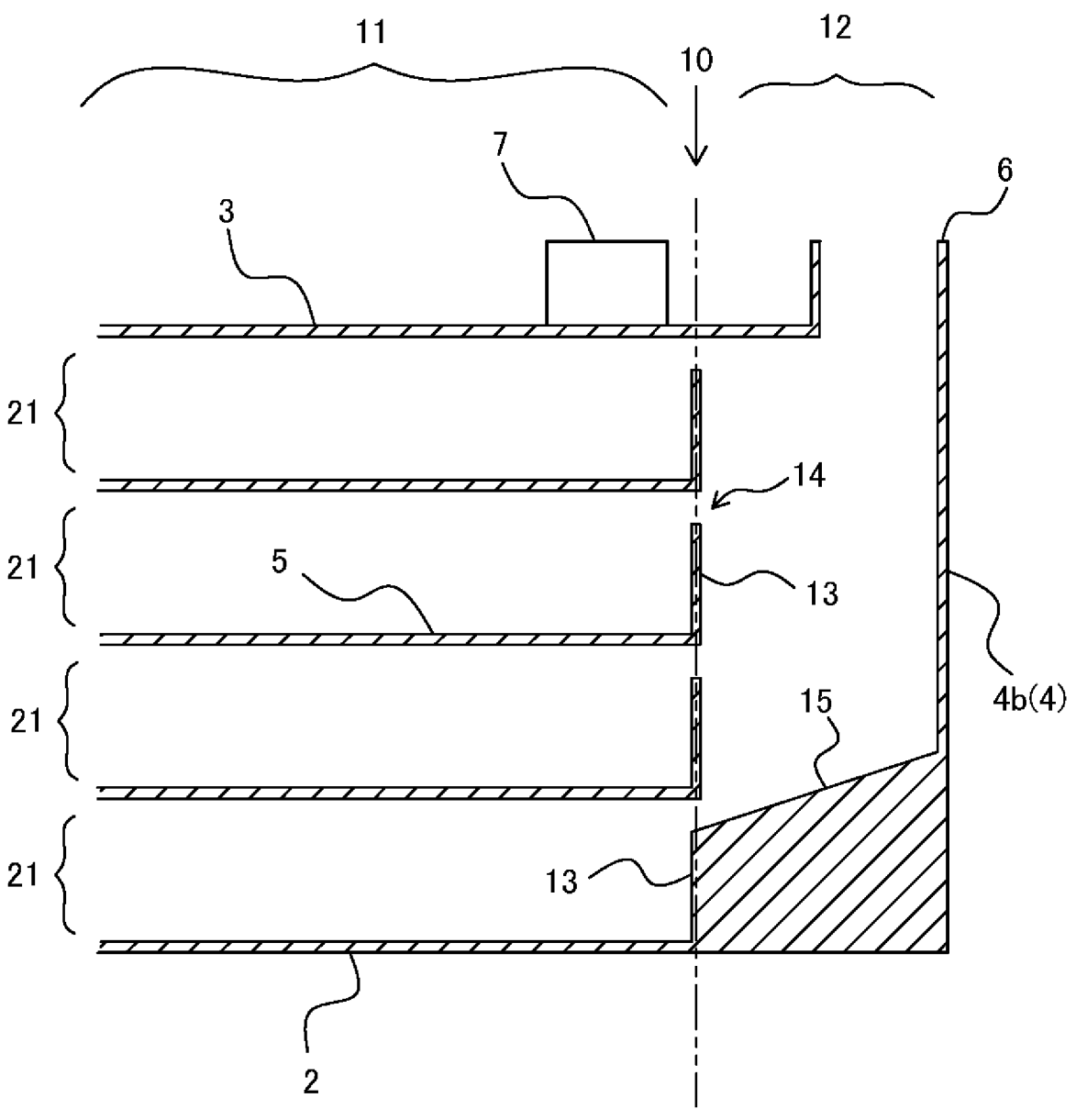
FIG. 2 is a cross-sectional view taken along line A-A in FIG. 1.

Further, communication portions 14 for bringing the culture layers 21 into communication with the buffer space 12 are formed between the entire upper ends of the wall portions 13 and the intermediate plates 5 or the top plate 3. Further, as shown in FIG. 2, there is provided an inclined plate 15 extending from the upper end of the wall portion 13 formed on the bottom plate 2 toward the side wall 4b on the other side while being inclined toward the top plate 3.

The liquid supply/drainage port 6 is an opening portion for supplying and draining a liquid to and from the multilayer culture vessel 1, and is formed in the top plate 3 at a location facing the buffer space 12 as shown in FIG. 1. Further, the liquid supply/drainage port 6 protrudes in a cylindrical shape, for example, and can be opened and closed by attaching and detaching a lid.

The exhaust port 7 is an opening portion for discharging a gas inside the multilayer culture vessel 1 and is formed in the top plate 3 at a location facing the culture space 11. Further, the exhaust port 7 protrudes in a cylindrical shape, for example, and can be opened and closed by attaching and detaching a lid. In addition, the liquid supply/drainage port 6 is formed closer to the side wall 4c than the exhaust port 7 in a direction from the side wall 4c toward the side wall 4d.

Subsequently, a procedure for supplying the peeling liquid 30 to the multilayer culture vessel 1 according to the present embodiment and peeling the cells will be described below with reference to FIGS. 3A to 3E. The same names are used for the postures like those of the conventional multilayer culture vessel shown in FIGS. 7A to 7D. Further, the hatched portion in FIGS. 3A to 3E is a region where the peeling liquid 30 exists.

Figure 3A:
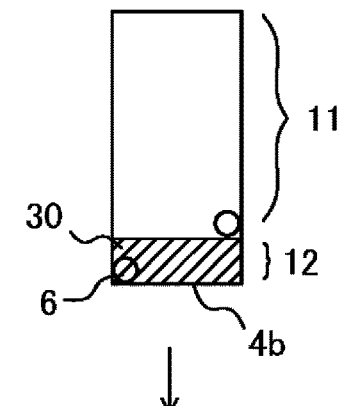
FIGS. 3A to 3E are diagrams illustrating a procedure for supplying a peeling liquid to the multilayer culture vessel and immersing cells in the peeling liquid.

First, the medium inside the multilayer culture vessel 1 is drained from the liquid supply/drainage port 6 in an opened state by causing the side walls 4b or 4c to be located on the bottom side. Subsequently, as shown in FIG. 3A, the multilayer culture vessel 1 is placed on the mounting surface so that the side wall 4b is located on the bottom side, i.e., so that the buffer space 12 is located on the bottom side (hereinafter referred to as storage posture), whereby the peeling liquid 30 is supplied to the buffer space 12 from the liquid supply/drainage port 6.

Figure 3B:
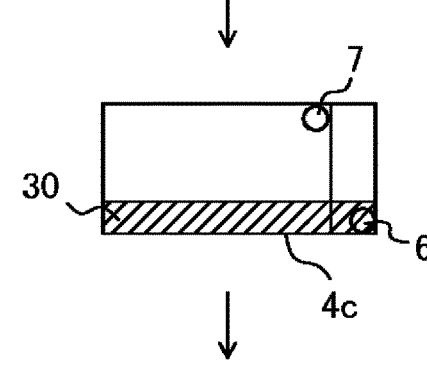
Figure 3C:
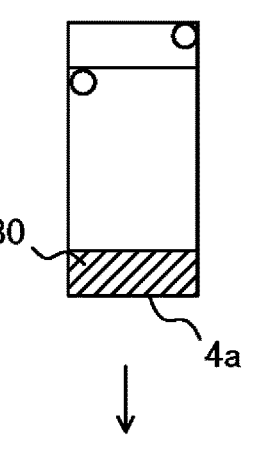
Figure 3D:
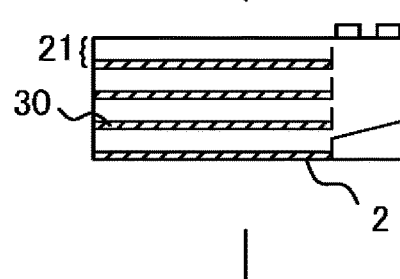
Figure 3E:
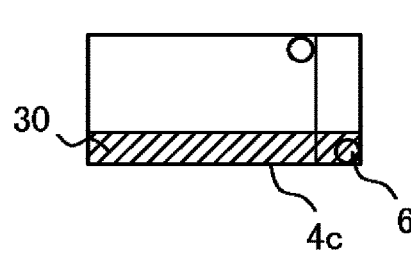

After the peeling liquid 30 is supplied, as shown in FIG. 3B, the multilayer culture vessel 1 is re-arranged on the mounting surface so that the side surface 4c is located on the bottom side (first posture). As a result, a part of the peeling liquid 30 stored inside the buffer space 12 flows into the respective culture layers 21 substantially evenly via the communication portions 14. Next, as shown in FIG. 3C, the multilayer culture vessel 1 is re-arranged on the mounting surface so that the side wall 4a is located on the bottom side, i.e., so that the culture space 11 is located on the bottom side (second posture). Thus, the entire peeling liquid 30 in the buffer space 12 flows into the respective culture layers 21 substantially evenly via the communication portions 14. Thereafter, as shown in FIG. 3D, by arranging the multilayer culture vessel 1 on the mounting surface so that the bottom plate 2 is located on the bottom side (third posture), the peeling liquid 30 in the respective culture layers spreads evenly along the bottom plate 2 or the intermediate plates 5. By leaving the multilayer culture vessel 1 at the third posture for a predetermined time, the cells are peeled from the bottom plate 2 and the intermediate plates 5. Then, as shown in FIG. 3E, the multilayer culture vessel 1 is arranged to be in the first posture at which the side surface 4c is located on the bottom side or the storage posture (FIG. 3A) at which the buffer space 12 is located on the bottom side, whereby the cells are discharged from the liquid supply/drainage port 6.

The internal space of the multilayer culture vessel 1 of the present embodiment is divided by the boundary surface 10 into the culture space 11 on one side and the buffer space 12 on the other side in the direction parallel to the bottom plate 2. Further, the multilayer culture vessel 1 includes the three intermediate plates 5 extending along the direction parallel to the bottom plate 2 and configured to divide the culture space 11 into four culture layers 21, the wall portions 13 arranged at the boundary surface 10 to extend from the bottom plate 2 and the three intermediate plates 5 in a direction toward the top plate 3, respectively, the four communication portions 14 configured to bring the buffer space 12 into communication with the respective culture layers 21, and the liquid supply/drainage port 6 formed in the top plate 3 at the location facing the buffer space 12.

By using the multilayer culture vessel 1 described above, the peeling liquid 30 can be supplied to the respective culture layers 21 by the following procedure. First, the multilayer culture vessel 1 is arranged on the mounting surface so that the side wall 4d on the other side is located on the bottom side, i.e., so that the buffer space 12 is located on the bottom side (storage posture). Subsequently, the peeling liquid 30 is supplied to the buffer space 12 from the liquid supply/drainage port 6. After the peeling liquid 30 is supplied, the multilayer culture vessel 1 is re-arranged on the mounting surface so that the side wall 4c is located on the bottom side, i.e., so that the bottom plate 2 and the intermediate plates 5 are arranged side by side in the horizontal direction (first posture). Thus, a part of the peeling liquid 30 inside the buffer space 12 flows into the respective culture layers 21 substantially evenly via the communication portions 14. Next, the multilayer culture vessel 1 is re-arranged on the mounting surface so that the side wall 4a is located on the bottom side, i.e., so that the culture space 11 is located on the bottom side (second posture). Thus, the entire peeling liquid 30 in the buffer space 12 flows into the respective culture layers 21 substantially evenly via the communication portions 14. Finally, when the multilayer culture vessel 1 is arranged on the mounting surface so that the bottom plate 2 is located on the bottom side (third posture), the peeling liquid 30 in the respective culture layers 21 spreads uniformly along the bottom plate 2 or the intermediate plates 5. According to the procedure described above, while the peeling liquid 30 is being supplied from the liquid supply/drainage port 6, the peeling liquid 30 flows into the buffer space 12 and does not flow into the respective culture layers 21. Further, when the multilayer culture vessel 1 is re-arranged twice at the first posture and the second posture after the supply of the peeling liquid 30, the peeling liquid 30 exists only in a partial region of each of the culture layers 21. However, such a re-arranging work can be completed in a short time. Therefore, the effect of time variance for the cells at different locations to be immersed in the peeling liquid 30 is small. That is, according to the present disclosure, by providing the buffer space 12 for temporarily storing the peeling liquid 30 when supplying the peeling liquid 30, it is possible to suppress the variations in the time for the cells to be immersed in the peeling liquid 30.

The multilayer culture vessel 1 of the present embodiment is provided with the inclined plate 15 extending from the upper end of the wall portion 13 formed on the bottom plate 2 toward the side wall 4d while being inclined toward the top plate 3. The peeling liquid 30 stored in the buffer space 12 then flows into the respective culture layers 21 via the communication portions 14. When the wall portion 13 is provided on the bottom plate, a part of the peeling liquid 30 remains in the portion of the buffer space 12 surrounded by the wall portion 13, the bottom plate 2, and the side surface 4d. Therefore, in the present embodiment, there is provided the inclined plate 15 extending from the upper end of the wall portion 13 provided on the bottom plate 2 toward the side wall 4d while being inclined toward the top plate 3. As a result, the peeling liquid 30 remaining in the buffer space 12 flows into the culture layer 21 between the bottom plate 2 and the intermediate plate 5 along the inclined plate 15. Therefore, the peeling liquid 30 remaining in the buffer space 12 can be reduced, and the peeling liquid 30 can be used without waste.

Figure 6:
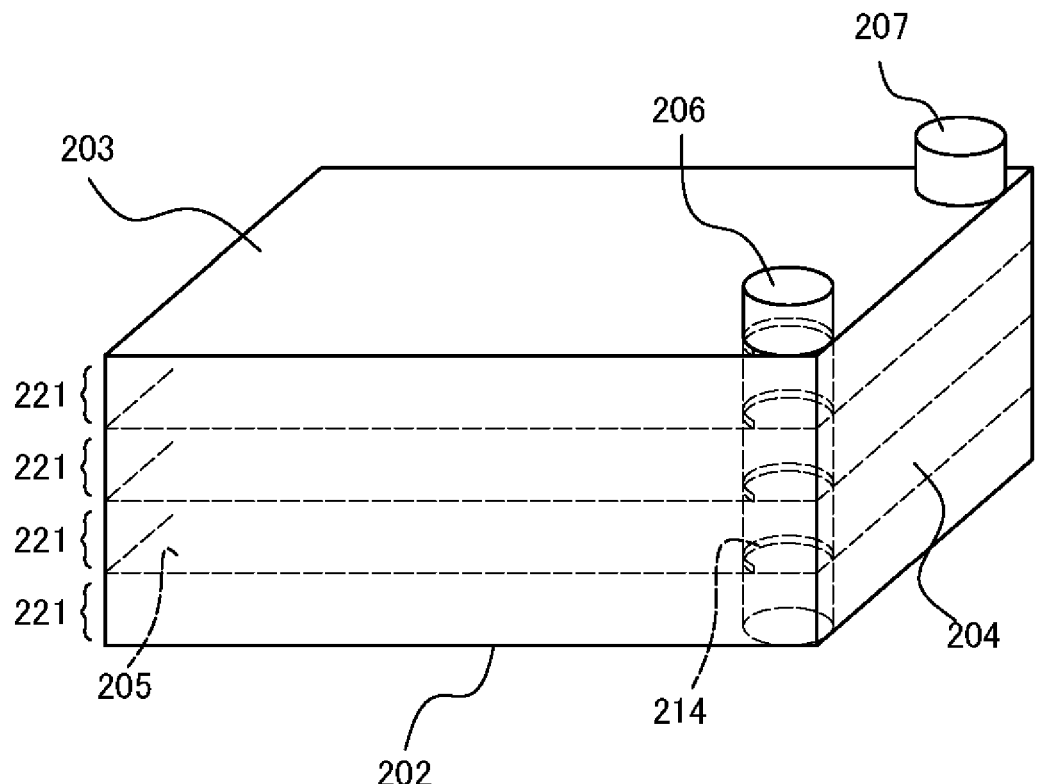
FIG. 6 is a perspective view showing a conventional multilayer culture vessel.
Figures 7A, 7B, 7C, 7D:
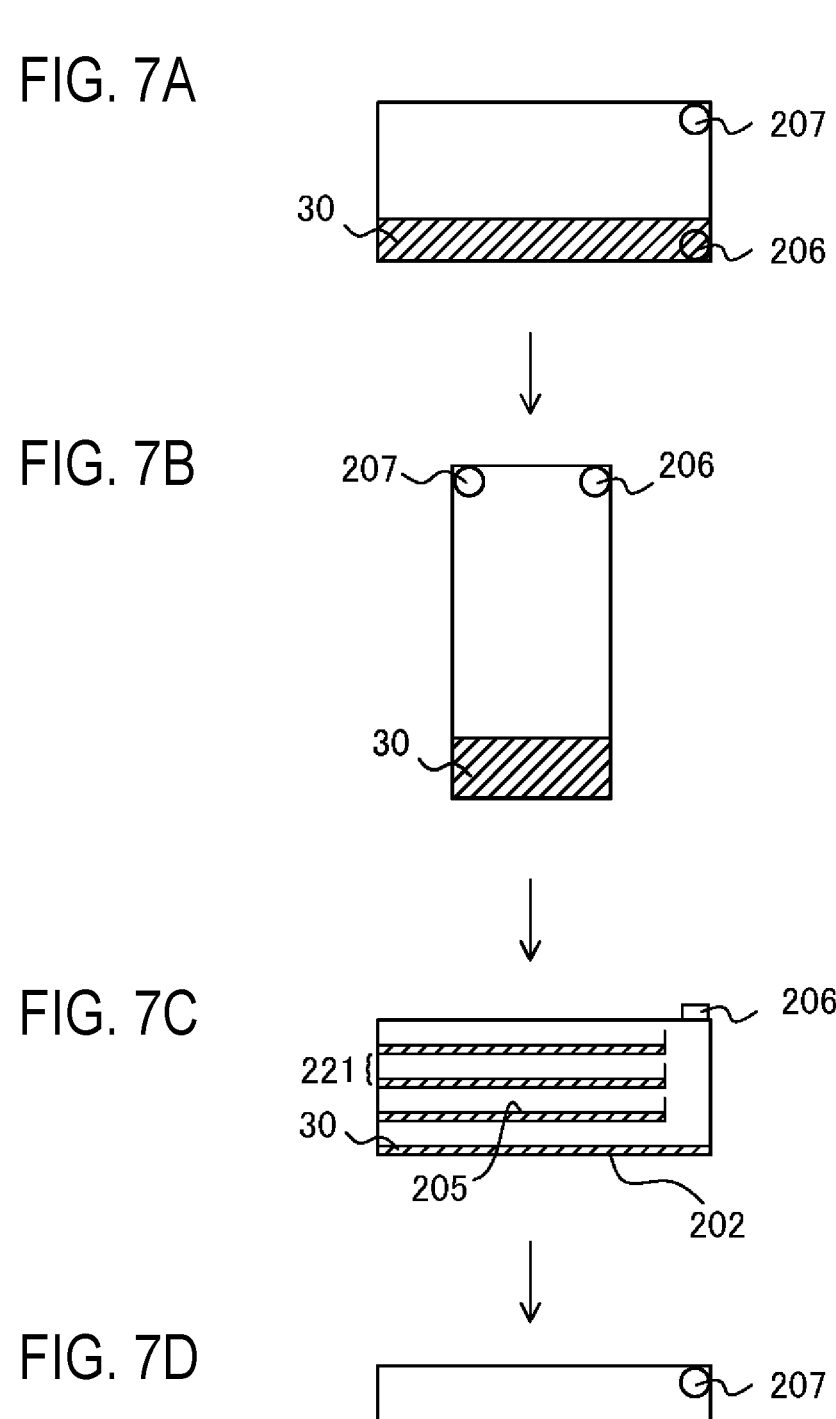
FIGS. 7A to 7D are diagrams illustrating a procedure for supplying a peeling liquid to the conventional multilayer culture vessel and immersing cells in the peeling liquid.

In the multilayer culture vessel 1 of the present embodiment, the three intermediate plates 5 extend to the boundary surface 10 in the culture space 11. In the conventional multilayer culture vessel 201, as shown in FIG. 6, the culture layers 221 are completely separated from one another by the intermediate plates 205. Therefore, in order to supply the peeling liquid 30 to the respective culture layers 221, it is necessary to provide the liquid supply/drainage part 206 that has a cylindrical shape penetrating the intermediate plates 205 and includes the plurality of communication portions 214 formed on the cylindrical side surface to communicate with the respective culture layers 221. In contrast, in the multilayer culture vessel 1 of the present embodiment, as shown in FIG. 1, the intermediate plates 5 extend to the boundary surface 10 in the culture space 11 on one side and do not extend to the buffer space 12 on the other side. That is, the buffer space 12 is not separated by the intermediate plates 5. The peeling liquid 30 supplied to the buffer space 12 can flow into the respective culture layers 21 via the communication portions 14 formed on the boundary surface 10. Therefore, according to the configuration of the present embodiment, in order to supply the peeling liquid 30 to the respective culture layers 21, it is sufficient to merely form an opening (liquid supply/drainage port 6) at a location facing the buffer space 12. The multilayer culture vessel 1 of the present embodiment can be easily manufactured as compared with the conventional multilayer culture vessel 201 which needs to form the cylindrical liquid supply/drainage part 206 penetrating the intermediate plates 205.

Although the preferred embodiment of the present disclosure has been described above, the present disclosure is not limited to this embodiment, and various modifications may be made as long as they are recited in the claims.

Figure 4:
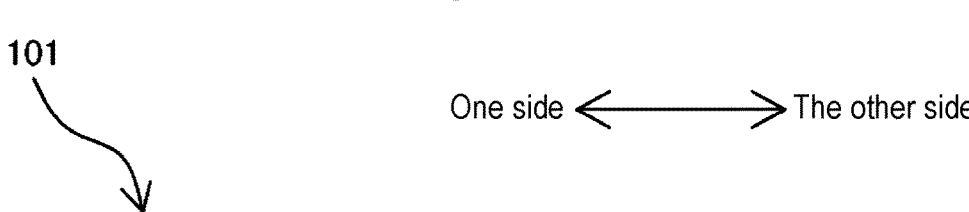
FIG. 4 is a perspective view showing a multilayer culture vessel according to a modification.
Figure 4:
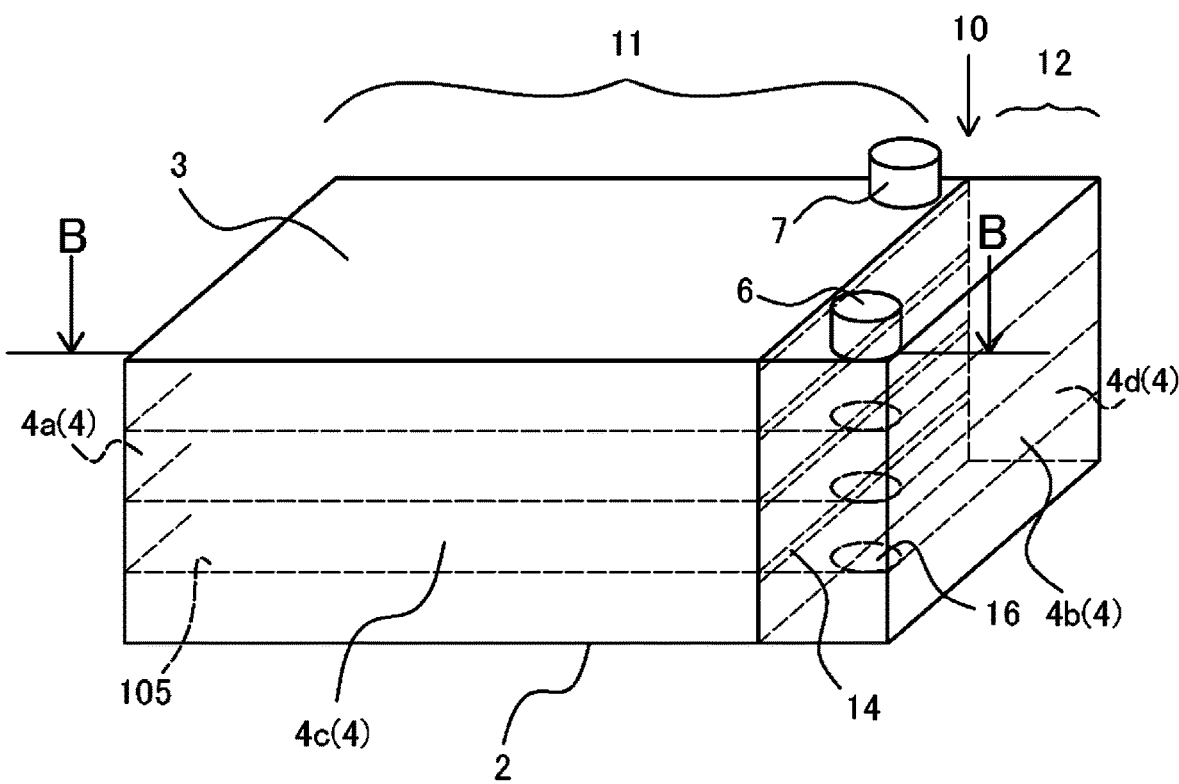
Figure 5:
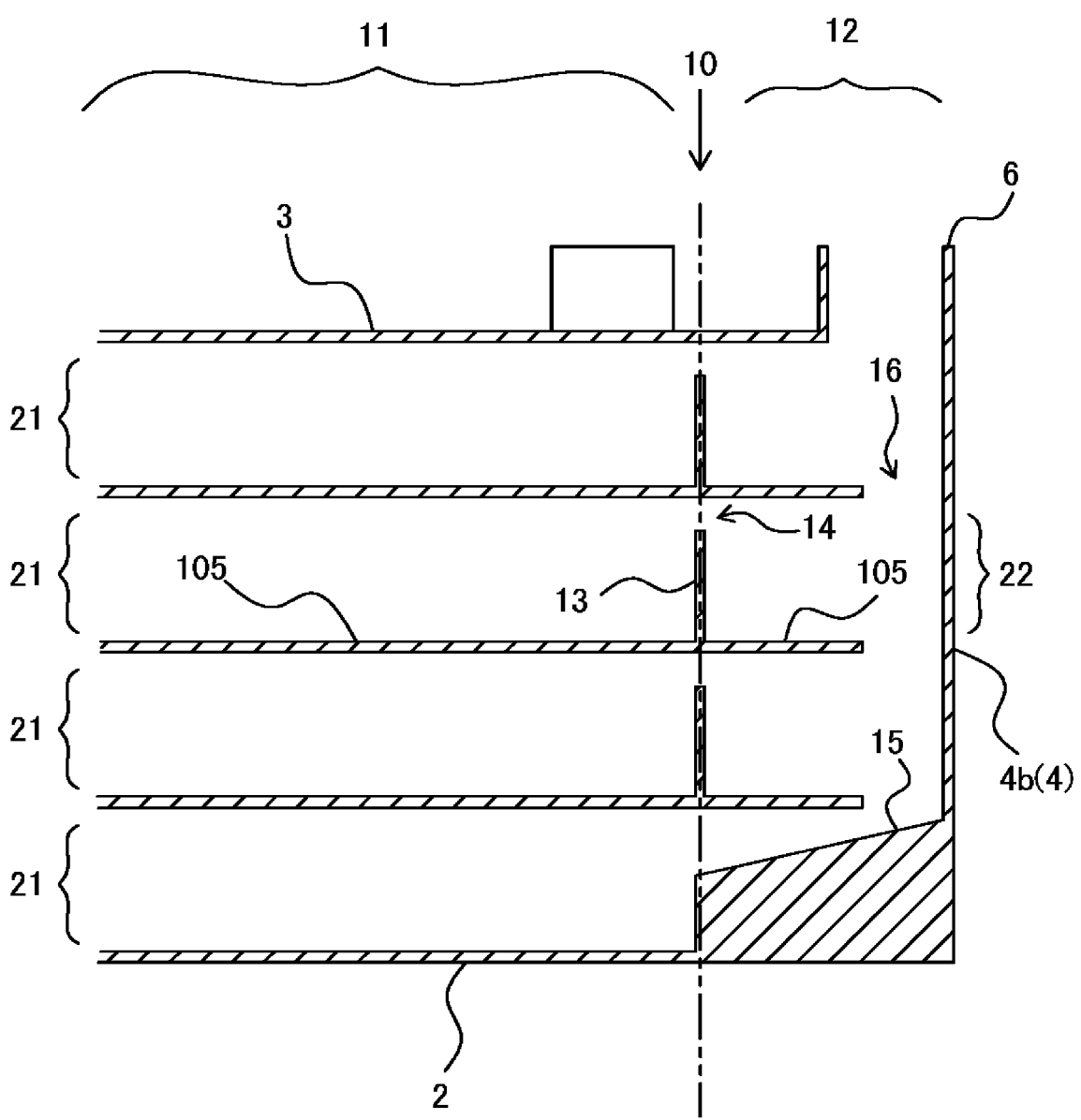
FIG. 5 is a cross-sectional view taken along line B-B in FIG. 4.

In the above-described embodiment, the intermediate plates 5 extend in the direction parallel to the bottom plate 2 inside the culture space 11 and make contact with the inner surfaces of the side walls 4a, 4c, and 4d. However, the intermediate plates 5 may extend along the direction parallel to the bottom plate 2 in both the culture space 11 and the buffer space 12. For example, in a multilayer culture vessel 101 according to a modification, as shown in FIGS. 4 and 5, the three intermediate plates 105 extend along the direction parallel to the bottom plate 2 and make contact with the inner surfaces of the side walls 4a, 4b, 4c, and 4d. In this case, the three intermediate plates 105 are formed with through-holes 16 penetrating the three intermediate plates 105 in the buffer space 12. According to this configuration, as shown in FIG. 5, the buffer space 12 is divided into four buffer layers 22 corresponding to the four culture layers 21 by the intermediate plates 105 extending to the side wall 4d.

Further, since the through-holes 16 are formed in the intermediate plates 105, a liquid or a gas can flow between the buffer layers 22. Therefore, when the peeling liquid 30 is supplied to the buffer space 12 and then the multilayer culture vessel is re-arranged on the mounting surface so that the side wall 4*c* is located on the bottom side (first posture), a part of the peeling liquid 30 flows into the respective culture layers 21 substantially evenly while the remaining part of the peeling liquid 30 is dividedly supplied into the buffer layers 22 substantially evenly and stored in the buffer layers 22. From this state, when the multilayer culture vessel 101 is re-arranged on the mounting surface so that the culture space 11 is located on the bottom side (second posture), the remaining part of the peeling liquid 30 stored substantially evenly in the respective buffer layers 22 flows into the respective culture layers 21 via the communication portions 14. Accordingly, the entire peeling liquid 30 can be more evenly supplied to the respective culture layers 21.

In the above-described modification, the intermediate plates 105 are in contact with the inner surface of the side walls 4*c* and 4*d*. However, the intermediate plates 105 may not be in contact with the inner surface of the side wall 4*b*. In this case, for example, the intermediate plates 105 extend to a location in the buffer space 12 between the boundary surface 10 and the side wall 4*b*. Further, in this case, since there is a gap between the intermediate plates 105 and the side wall 4*b*, the through-holes 16 for allowing a liquid or a gas to flow between the buffer layers are unnecessary.

In the above-described embodiment and the above-described modification, three intermediate plates are arranged. Alternatively, one or two intermediate plates, or four or more intermediate plates may be arranged.

Further, in the above-described embodiment, at the boundary surface 10, the wall portions 13 extend from the bottom plate 2 and from each of the intermediate plates 5 toward the top plate 3 in the direction perpendicular to the bottom plate 2 and the intermediate plates 5. However, the wall portions 13 may be inclined to one side or the other side. Further, each of the communication portions 14 may be formed between a part of the upper end of each of the wall portions 13 and each of the intermediate plates 5 or the top plate 3. In this case, the remaining part of the upper end of each of the wall portions 13 where each of the communication portions 14 is not formed is in contact with the intermediate plates 5 or the top plate 3. Alternatively, the entire upper end of each of the wall portions 13 is in contact with the intermediate plates 5 or the top plate 3, and one or more communication portions 14 may be formed at an arbitrary location in the wall portions 13.

In the above-described embodiment, the liquid supply/drainage port 6 is formed in the top plate 3 at the location facing the buffer space 12. However, the liquid supply/drainage port 6 may be formed on the side walls 4*b*, 4*c*, or 4*d* at a location facing the buffer space 12.

In the above-described embodiment, the exhaust port 7 is formed in the top plate 3 at the location facing the culture space 11. However, the exhaust port 7 may be formed in the side walls 4*a*, 4*b*, 4*c*, or 4*d* at a location facing the culture space 11 or the buffer space 12.

In the above-described embodiment, the cells are peeled from the bottom plate 2 and the intermediate plates 5 by leaving the multilayer culture vessel added with the peeling liquid in the third posture for a predetermined time. However, for example, after leaving the multilayer culture vessel 1 in the third posture for a predetermined time, the multilayer culture vessel 1 may be tapped to peel the cells from the culture layers. In this case, it becomes easier to peel the cells than when the multilayer culture vessel 1 is merely left for a predetermined time.

In the above-described embodiment, the bottom plate 2 and the top plate 3 have a rectangular shape. However, the bottom plate 2 and the top plate 3 may have a trapezoidal shape, other polygonal shapes, an elliptical shape, or a combination thereof.

EXPLANATION OF REFERENCE NUMERALS

1, 101: multilayer culture vessel, 2: bottom plate, 3: top plate, 4, 204: side wall, 5, 105, 205: intermediate plate, 6: liquid supply/drainage port, 7: exhaust port, 10: boundary surface, 11: culture space, 12: buffer space, 13: wall portion, 14: communication portion, 15: inclined plate, 16: through-hole, 21, 221: culture layer

What is claimed is:

1. A multilayer culture vessel capable of culturing cells in a plurality of culture layers, the multilayer culture vessel comprising:
   a housing including a bottom plate, a top plate facing the bottom plate, and a plurality of side walls, which includes at least a first side wall and a second side wall opposite to the first side wall, connecting the bottom plate and the top plate;
   a boundary portion that divides an internal space of the housing into a culture space on one side of the boundary portion and a buffer space on the other side of the boundary portion in a first direction parallel to the bottom plate;
   at least one intermediate plate extending along the direction parallel to the bottom plate at least in the culture space and configured to divide the culture space into the plurality of culture layers;
   a plurality of wall portions at the boundary portion, the plurality of wall portions including one extending from the bottom plate in a direction toward the top plate and one extending from each of the at least one intermediate plate in a direction toward the top plate;
   a plurality of communication portions formed at the boundary portion to bring the culture layers into communication with the buffer space;
   a liquid supply/drainage port formed on the top plate of the housing at a location facing the buffer space; and
   an exhaust port that is formed, separately from the liquid supply/drainage port, on the top plate at a location facing the culture space,
   wherein the liquid supply/drainage port is arranged adjacent to the first side wall and the exhaust port is arranged adjacent to the second side wall, and
   wherein the first side wall and the second side wall are opposite to each other in a second direction perpendicular to the first direction.

2. The multilayer culture vessel of claim 1, further comprising an inclined plate extending from an upper end of the wall portion formed on the bottom plate toward the side wall that is on the other side of the boundary portion while being inclined toward the top plate.

3. The multilayer culture vessel of claim 2, wherein the at least one intermediate plate extends to the boundary portion in the culture space.

4. The multilayer culture vessel of claim 2, wherein the at least one intermediate plate extends along the direction parallel to the bottom plate in both the culture space and the buffer space to divide the buffer space into a plurality of buffer layers, and wherein a through-hole penetrating the at least one intermediate plate is formed in the buffer space.

5. The multilayer culture vessel of claim 1, wherein the at least one intermediate plate extends to the boundary portion in the culture space.

6. The multilayer culture vessel of claim 1, wherein the at least one intermediate plate extends along the direction parallel to the bottom plate in both the culture space and the buffer space to divide the buffer space into a plurality of buffer layers, and wherein a through-hole penetrating the at least one intermediate plate is formed in the buffer space.

7. A cell culture method by using the multilayer culture vessel of claim 1, wherein the plurality of side walls includes a first sidewall placed on a side of the culture space, a second sidewall opposite to the first sidewall and placed on a side of the buffer space, a third sidewall connected to the first sidewall and the second sidewall, and a fourth sidewall opposite to the third sidewall, wherein the cell culture method comprises:

placing the multilayer culture vessel in a storage posture with the second sidewall located on the bottom side;

supplying a peeling liquid to the buffer space via the liquid supply/drainage port;

placing the multilayer culture vessel in a first posture with the third sidewall located on the bottom side;

placing the multilayer culture vessel in a second posture with the first sidewall located on the bottom side;

placing the multilayer culture vessel in a third posture with the bottom plate located on the bottom side; and placing the multilayer culture vessel in the storage posture or the first posture so that the cells in the plurality of culture layers are discharged via the liquid supply/drainage port.

8. The method of claim 7, wherein a time period for which the multilayer culture vessel is in the third posture is longer than a time period for which the multilayer culture vessel is in the second posture.

\* \* \* \* \*